United States Patent
Aebi et al.

(10) Patent No.: US 8,701,955 B2
(45) Date of Patent: Apr. 22, 2014

(54) PIN CUTTING TOOL

(75) Inventors: This Aebi, Grenchen (CH); Robert Dominik, Commugny (CH)

(73) Assignee: Stryker Trauma SA (CH)

( * ) Notice: Subject to any disclaimer, the term of this patent is extended or adjusted under 35 U.S.C. 154(b) by 494 days.

(21) Appl. No.: 12/872,066

(22) Filed: Aug. 31, 2010

(65) Prior Publication Data

US 2011/0062204 A1    Mar. 17, 2011

(30) Foreign Application Priority Data

Sep. 11, 2009   (EP) ..................................... 09170070

(51) Int. Cl.
*A61B 17/88*   (2006.01)
*B23D 29/02*   (2006.01)

(52) U.S. Cl.
USPC .......................................... 225/103; 606/180

(58) Field of Classification Search
USPC ............ 30/93, 94, 95, 97; 606/170, 171, 180; 82/46, 70.1, 70.2, 73, 76; 225/103
See application file for complete search history.

(56) References Cited

U.S. PATENT DOCUMENTS

| | | | |
|---|---|---|---|
| 3,315,669 A * | 4/1967 | Rhodes | 606/101 |
| 5,513,434 A | 5/1996 | Hamman | |
| 5,669,923 A * | 9/1997 | Gordon | 606/170 |
| 5,980,547 A | 11/1999 | Rinner | |
| 6,085,425 A | 7/2000 | Weber | |
| 6,860,888 B2 * | 3/2005 | Ball et al. | 606/104 |
| 6,928,900 B2 | 8/2005 | Dall et al. | |
| 2005/0149086 A1 | 7/2005 | Huxel et al. | |
| 2006/0149290 A1 | 7/2006 | Matthys-Mark et al. | |

FOREIGN PATENT DOCUMENTS

| | | |
|---|---|---|
| DE | 19853917 A1 | 5/2000 |
| WO | 2008073949 A1 | 6/2008 |

* cited by examiner

*Primary Examiner* — Stephen Choi
(74) *Attorney, Agent, or Firm* — Lerner, David, Littenberg, Krumholz & Mentlik, LLP (57) ABSTRACT

A tool for breaking a shaft has a first and a second tubular element, both provided with inner through bores adapted to receive a shaft in the tool. A first handle is fixedly connected with the first tubular element and the second tubular element is connected to a second handle. A bottom surface of the second tubular element forms a shearing plane with a neck surface of the first tubular element. A rotation between the two tubular elements shears the shaft at the shearing plane. The second handle turns the first tubular element around an axis and has a gear engaging the second tubular element for transmitting the rotation of the second handle into a rotation of the second tubular element. The drive element is mounted offset, in a direction of the longitudinal axis, from the gear.

28 Claims, 6 Drawing Sheets

PIN CUTTING TOOL

BACKGROUND OF THE INVENTION

The present invention relates to a tool for breaking a shaft of a surgical pin or screw, e.g. a Schanz-type screw, in order to reduce the excess portion of the pin extending beyond a fixator in bone surgery.

External fixators are widely used in bone surgery in order to reduce the fracture of a bone and to maintain the bone fragments in a fixed relationship. Commonly, pins are inserted into the bone for connection to the fixator. Such pins and/or screws often are of an undefined or uniform length, making it desirable for their excess shaft portions projecting beyond an exposed surface to be removed. For this purpose, various pin cutter devices have been developed.

For instance, U.S. Pat. No. 6,085,425 relates to a surgical cutter having two cooperating jaws pivotally secured in between two holding plates by floating bolts, and having said jaws pivotally secured to two very long handles in order to build up the large leverage force necessary.

U.S. Pat. No. 5,513,434 relates to a pin cutter with a cutting wheel for forming an annular groove about the periphery of the pin. Therefore, the surgical pin is positioned between cylindrical rollers and the cutting wheel. A thumb wheel is turned onto external threads of an internal sleeve, causing the sleeve to be drawn further into the cutter housing for increased compression of the cutting wheel into the pin. A camming surface of the housing contacts externally flared walls of a pair of spaced legs on the distal end of the cutter. By the movement of the sleeve, the legs are biased inwardly, causing the cutting wheel to push further into the pin. Handles are used to rotate the cutter wheel to deepen the groove in the periphery of the pin. Thereby, the pin can be completely severed or, alternatively, snapped at the line of the peripheral groove formed by the cutter.

DE 198 53 917 A1 discloses a pin cutter incorporating shearing elements driven by a rotary piston unit which is operated by a control valve. A billet-shaped handle coaxial with the longitudinal axis of the housing is positioned on the top housing-cover. The top end of the operating valve is integrated in the handle. The bottom housing cover has a holder for the plug-in connection for a cutter-head. The handle has a hole containing the projecting pin as an extension of the rotor's hollow shaft, the bottom end of which has an inner hexagonal part forming a drive connection with the shearing-pin. With this construction, the user does not have to incur large manual forces but can activate the device by pressing an actuation button. It is difficult to include such a compressed air using device in a surgical setting because maintenance and sterilization issues.

The shearing tool of U.S. Pat. No. 6,928,900 allows a threaded shaft, such as that of a screw, to be cleanly broken along a line by twisting contiguous shaft portions against each other. The device comprises two aligned tubular, preferably telescopically engaged elements, each having an end portion for receiving a contiguous portion of a shaft and being locked against rotation relative to the shaft portion contained therein. In order to relatively twist the shaft portions, the tubular elements are rotated relative to each other. The rotating means comprises two arms extending laterally from the common axis of the elements. By bringing together and forcing back the arms repeatedly, the shaft is ultimately fractured. This device allows the shaft to be sheared at their interface, achieving a substantially planar surface at the fracture plane.

BRIEF SUMMARY OF THE INVENTION

For manual devices as the one disclosed in U.S. Pat. No. 6,928,900, in order to develop the high shearing forces necessary, often, long levers are used. However, by actuating both levers, unwanted forces can sometimes be transferred to the pin.

Furthermore, the use of two large handles may result in an undesired rotation of the screw. This can be overcome by keeping one handle in place and moving only the second handle. However, such a construction is not user friendly and leads to mistakes.

The present invention overcomes the above mentioned disadvantages by providing a pin cutter instrument wherein one handle is stationary for holding the instrument in place, and only the second handle is designed to be turned.

The tool for breaking a shaft comprises a first and a second tubular element, both provided with inner through bores adapted to receive a first and second portion of said shaft in a parking position of the tool. A first handle is fixedly connected with the first tubular element, wherein the second tubular element is connected to a second handle. A bottom surface of the second tubular element is in contact with a neck surface of the first tubular element forming a shearing plane perpendicular to the main axis of the tool. Starting from a parking position, a rotation between the two tubular elements around this axis creates a twisting movement of the two shaft portions received in the two tubular elements, respectively, and shears the shaft portions at the interface between them. The second handle is a turning handle mounted on the first tubular element for a rotation around an axis and comprising a gear engaging the second tubular element for transmittal of a rotation of the turning handle into a rotation of the second tubular element for said twisting movement.

Thereby, only portion of shaft rotated which is not received in the bone—thereby maintaining a strong connection between the shaft/screw and the bone and/or fixator. There is no mutual relative twist, only one shaft length twisted against the other.

It is a further aspect of the invention to provide an easy pin cutter tool for Schanz screws comprising a grooved rod portion to be cut.

These and other aspects of the invention are achieve by a tool for breaking a shaft having a first tubular element comprising an inner through bore adapted to receive a first portion of said shaft in a first position of the tool. A second tubular element has an inner through bore adapted to receive a further second portion of the shaft in the first position of the tool. A first handle and a second handle are provided wherein the first tubular element is connected to the first handle, wherein the second tubular element is connected to the second handle. A longitudinal axis of said first tubular element, a longitudinal axis of said second tubular element as well as an axis of the shaft to be broken are parallel one to the other. The second tubular element has a bottom surface being in contact with a neck surface of the first tubular element forming a shearing plane perpendicular to said parallel axes.

Starting from the first position, a rotation between the first tubular element and the second tubular element around one of their longitudinal axes creates a twisting movement of the second shaft portion received in the second tubular element relative to the first shaft portion received in the first tubular element and shears the shaft portions at the interface between them. The first handle is fixedly connected to the first tubular element, the second handle is a turning handle mounted on the first tubular element for a rotation around an axis parallel to said longitudinal axis of the shaft. A gear engages the second tubular element for transmittal of a rotation of the turning handle into a rotation of the second tubular element for the twisting movement.

The turning handle comprises an axle having a gear mounted to mesh with a transmission gear mounted with the second tubular element. The gear is a cogwheel having a toothed sector covering an angle of between 45 and 120 degrees. The turning handle is mounted on the first handle and a spring is mounted between the first tubular element and the second tubular element is adapted to rotate the second tubular element into said first position. The spring is arranged within the first tubular element and concentrically with the second tubular element. The inner through bore of the first tubular element is adapted to receive the first portion of the shaft and is coaxially aligned along a longitudinal axis of the tool. The inner through bores of the first and second tubular elements comprise positive locking elements are adapted to lock each shaft portion against rotation relative to the shaft itself, wherein said positive locking elements are aligned in the first position.

The turning handle is rotatable about a rotational axis arranged parallel to and offset from the longitudinal axes of the first and second tubular elements. The first tubular element comprises a first insert having the inner through bore adapted to receive said first portion of the shaft and the second tubular element comprises a second insert having the inner through bore adapted to receive the further second portion of said shaft. The first insert and the second insert have juxtaposed surfaces for a positive fit with the first and second tubular element, respectively. The shearing rotation is actuated around the longitudinal axis of the pin, wherein the inner through bore of the first tubular element provides a first positive fit for one portion of a pin to be introduced and said inner through bore of the second tubular element which provides a second positive fit for another portion of said pin to be introduced. The positive fit is adapted to lock each shaft portion against rotation relative to the shaft itself. The gear comprises a reduction gear and the first tubular element comprises at least one inner through bore along an axis eccentric relative to the longitudinal axis of the first tubular element. The second tubular element comprises, in the first position, at least one corresponding inner through bore along an axis eccentric relative to the longitudinal axis of the first tubular element. The first tubular element comprises one inner through bore along the longitudinal axis of the first tubular element. The second tubular element comprises, in a parking position, at least one corresponding inner through bore along the first tubular element axis. The longitudinal axis of the second tubular element is eccentric relative to the longitudinal axis of the first tubular element.

Other aspects are provided by a tool for breaking a shaft having a first tubular element having a bore for receiving a first shaft portion extending along a longitudinal axis a second tubular element is provided having a bore for receiving a second shaft portion extending along a longitudinal axis rotatably mounted with respect to the first tubular element. A first handle connected to the first tubular element and a second handle connected to the second tubular element. The longitudinal axis of the first tubular element, the longitudinal axis of the second tubular element as well as a longitudinal axis of the shaft to be broken are parallel one to the other. A surface of the second tubular element is in contact with a surface of the first tubular element forming a shearing plane perpendicular to the parallel axes.

Starting from a first position, a rotation between the first tubular element and the second tubular element around one of these axes creates a relative movement between the second shaft portion received in the second tubular element bore and the first shaft portion received in the first tubular element bore thereby shearing the shaft portions at the shearing plane. A first handle is mounted on the first tubular element for a rotation of the first tubular element around the first longitudinal axis. A gear engages the second tubular element for transmittal of a rotation of a second handle to the second tubular element for producing the relative movement. The second handle comprises an axle having a gear mounted thereon to mesh with the gear mounted with the second tubular element. A transmission gear is a cogwheel covering an angle of between 45 and 120 degrees. A spring is mounted between the first tubular element and the second tubular element adapted to rotate the second tubular element into said first position. The spring is a leg-spring arranged within the first tubular element and concentrically with the second tubular element. The bore of the first tubular element is adapted to receive the first portion of the shaft is coaxially aligned along a longitudinal axis of the tool. The inner through bores of the first and second tubular elements further comprise positive locking elements adapted to lock each shaft portion against relative rotation. The positive locking elements are aligned in a first position to allow insertion of the shaft. The second handle is rotatable about a rotational axis arranged parallel to the longitudinal axes of the first and second tubular elements. The rotational axis of the second handle is arranged parallel and offset to the longitudinal axes of the first and second tubular elements. The first tubular element comprises a first insert having the through bore adapted to receive the first shaft portion and wherein the second tubular element comprises a second insert having the bore adapted to receive the second shaft portion. The first insert and the second insert have juxtaposed surfaces producing a positive fit with the first and second tubular element respectively. The shearing rotation is actuated around the longitudinal axis of the pin. The bore of the first tubular element provides a first positive fit for a first shaft portion of a pin to be introduced in the tool and the bore of the second tubular element provides a second positive fit for a second shaft portion of the pin to be introduced in the tool. The positive fit is adapted to lock each shaft portion against rotation. The gear is a reduction gear and the first tubular element comprises at least one inner through bore along an axis eccentric relative to the longitudinal axis of the first tubular element. The second tubular element comprises, in the first position, at least one corresponding inner through bore along an axis eccentric relative to the longitudinal axis of the first tubular element. The first tubular element comprises one inner through bore along the longitudinal axis of the first tubular element. The second tubular element comprises, in the first position, at least one corresponding inner through bore along the first tubular element longitudinal axis, wherein a longitudinal axis of the second tubular element is eccentric relative to the longitudinal axis of the first tubular element.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings.

DETAILED DESCRIPTION

Figure 1:
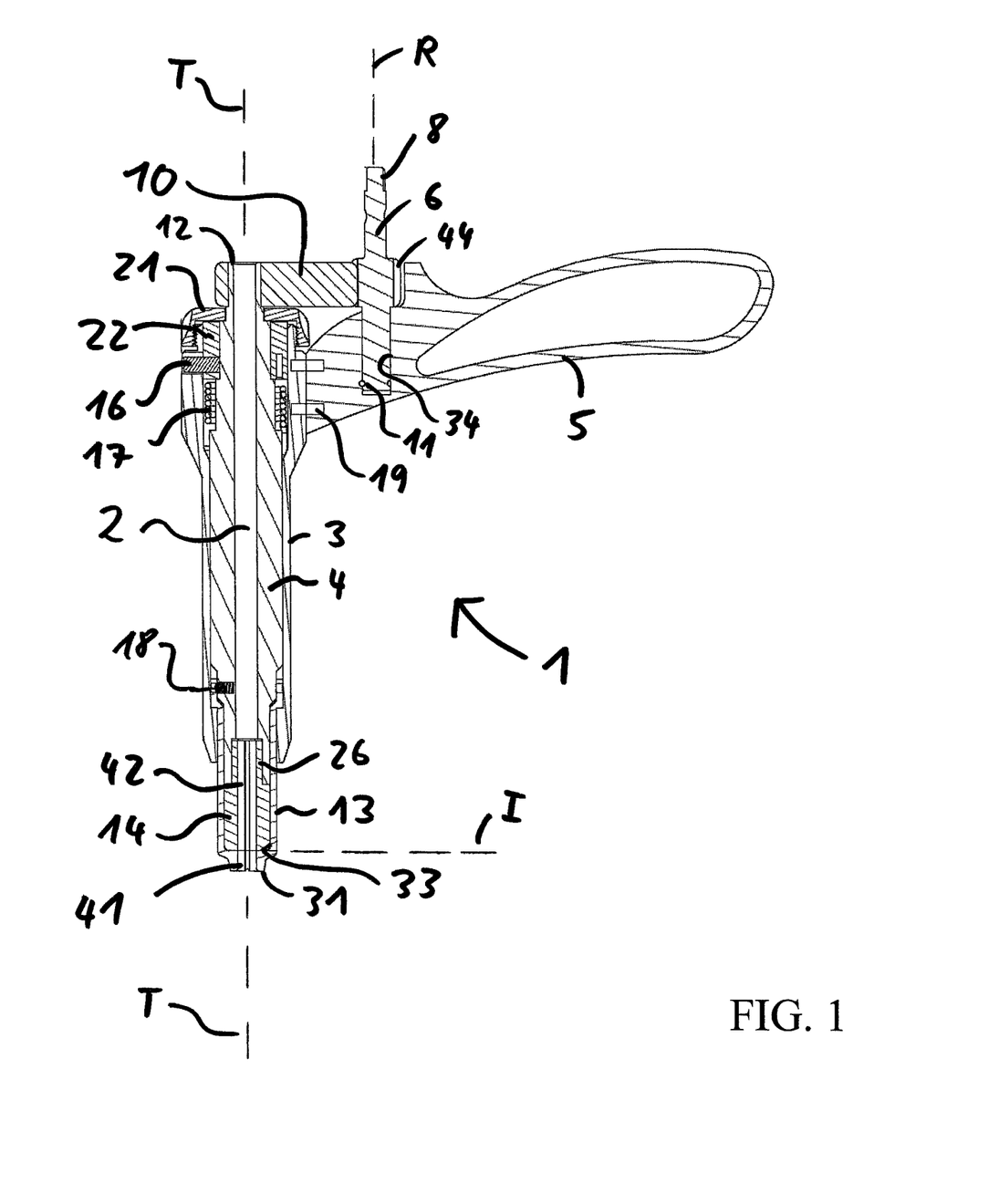
FIG. 1 shows a cross-section of a pin cutter according to a first embodiment of the invention, omitting the handle of the cutter.
Figure 2:
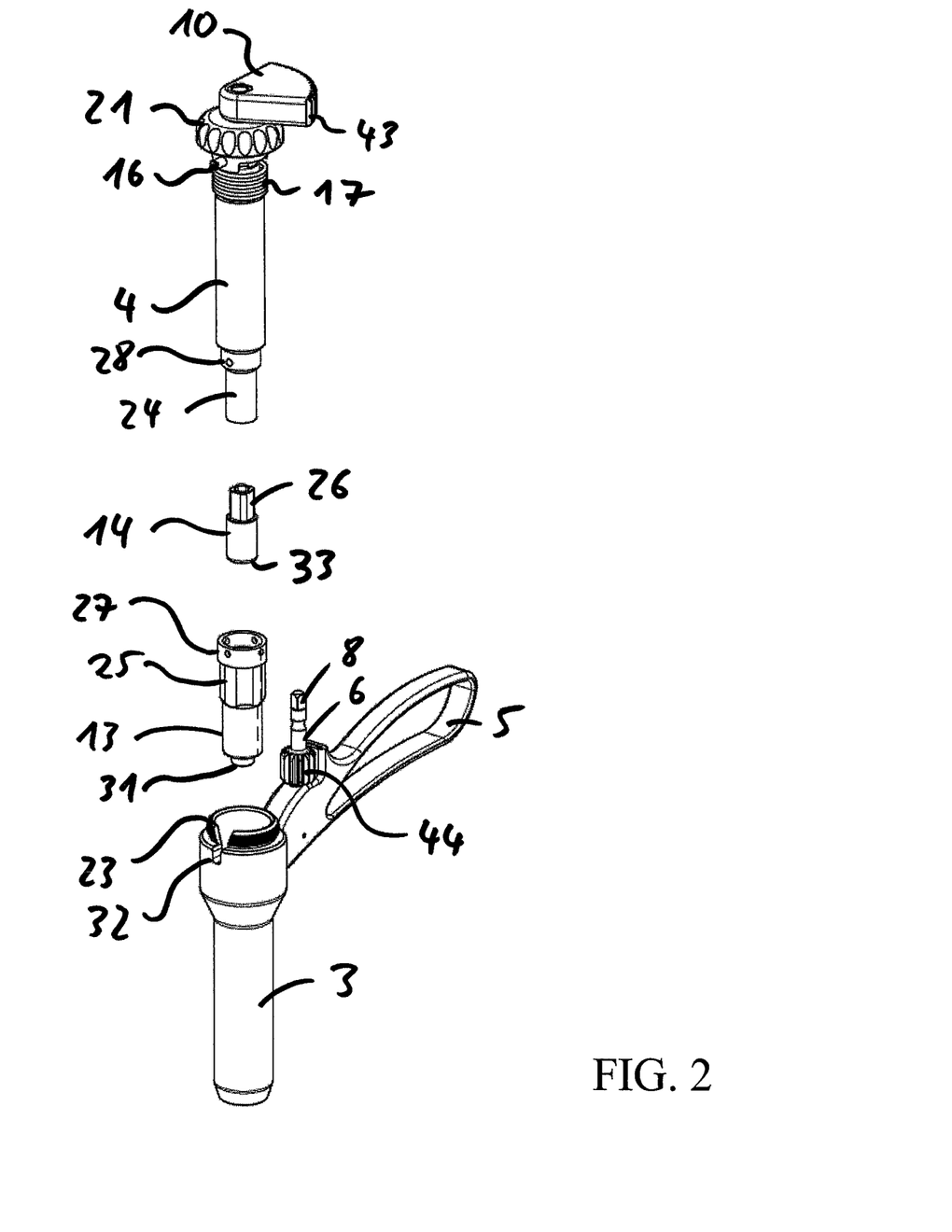
FIG. 2 shows an exploded perspective view of the cutter according to FIG. 1.

Referring to FIGS. 1 and 2, there is shown a cross-section of a pin cutting tool or pin cutter 1, i.e. a tool for breaking a shaft of a pin with or without a screw, according to a first embodiment of the invention, which embodiment omits the turning handle or crank 7 (see FIG. 4) of the cutter 1. FIG. 1 is explained in connection with FIG. 2 showing an exploded perspective view of the cutter. A pin or screw (not shown) to be shortened is to be introduced into the through bore 2, defining the longitudinal axis T of the cutter 1. The through bore 2 being defined through introduction of several components as explained below has a remaining inner cavity and dimension to accommodate a pin. The pin, which is to be broken, is usually already introduced in bone material and fixed. The longitudinal axis of the pin is also the axis T and the cutter 1 has to be positioned accordingly on such a pin.

The cutter 1 comprises a stationary portion and a rotating portion.

The stationary portion comprises a first tubular element 3 attached to a holding handle 5 comprising fastening screws 19 to connect these two parts. It is of course possible to provide an outer first tubular element 3 unitary with the handle 5. The first tubular element 3 comprises an insert as first gripping component or insert 13 comprising outer juxtaposed surfaces 25 as can be seen in FIG. 2. The surfaces 25 have complementary surfaces on the inside of tubular element 3 allowing a positive fit connection. As it can be seen from FIG. 2 insert 13 can be introduced from the distal end, i.e. the end near the handle 5 of the cutter 1 into the through bore 2. The lower end of the insert 13 defines the nozzle 31 of the cutter 1. Lower surface of the cutter 1 can be positioned on a nut or bone plate or can be positioned at a different height along the pin.

A through bore 41 within the first gripping element 13 comprises, in this first embodiment, a cylindrical inner wall comprising at least one rib, e.g. four ribs 9 as shown in FIG. 2. The cylindrical inner wall defines the diameter of the pin or screw to be sectioned wherein the screw comprises at least one longitudinal groove allowing a positive fit between the insert 13 and thus the stationary portion of the cutter 1 and the screw shaft. The embodiment shown comprises four ribs and the screws to be sectioned with this insert have a corresponding diameter and four longitudinal grooves. Of course it is also possible to provide grooves in the insert 13 and ribs on the screw shafts. It is only important that the shaft of the screw is in a positive fit with the insert 13. In order to section shafts of different screws (different diameter, different outer form), the insert 13 can be replaced as shown in FIG. 2. In another embodiment the end portion of each tubular element 3 and 4 has a non-circular opening for receiving the shaft of the pin for restricting rotation therein of a shaft with a correspondingly non-circular cross-section.

Furthermore, the stationary portion comprises a closing screw coupling 21 having an inner thread which can be screwed on the outer thread 23 of the first tubular element 3. Closing coupling 21 is pre-mounted on the rotating portion together with the intermediate element 22 comprising a holding pin 16.

The rotation portion comprises a second tubular element 4 to be introduced from the distal end into the first tubular element 3 and then held in place by turning the screw coupling 21. The holding pin 16 is pushed into peripheral opening 32 of the first tubular element 3 and thus blocked against any rotation. A spring 17, such as a coil spring, is provided around the second tubular element 4 and engages tubular element 4 as well as intermediate element 22. Therefore the fixed intermediate element 22 in first tubular element 3 provides together with the spring 17 a stationary or parking position and any rotation of the inner second tubular element 4 is achieved against the elastic force of spring 17 ensuring that after using the cutter 1 the two tubular elements come back in their starting position, which provides an advantage in view of the positive fit as explained below. In an alternate embodiment the spring 17 can be omitted.

The second tubular element 4 is inserted coaxial to the axis T in the first tubular element 3. The second tubular element 4 comprises a reduced diameter portion 24 receiving an insert as second gripping component 14 comprising outer juxtaposed surfaces 26 as can be seen in FIG. 2. The surfaces 26 have complementary surfaces on an inside of tubular element 4 within the reduced diameter portion 24 allowing a positive fit connection between these elements. As it can be seen from FIG. 2 insert 14 can be introduced from the distal end into outer tubular element 3 after introduction of the stationary insert 13 into the through bore 2. In view of the positive fit elements 4 and 14 can be pre-mounted. The lower end of the insert 14 abuts against the upper end surface of insert 13 and defines the plane I of the shearing surface, shown as a line in the drawing plane of FIG. 1. In other words, the shearing plane surface 33 of the insert 14 abuts against a corresponding upper surface or neck of insert 13 defining plane I.

A through bore 42 within the second gripping element 14 comprises, in this first embodiment, a cylindrical inner wall comprising a number of ribs 9 which is, in a preferred embodiment, equal to the number of ribs within the first gripping element 13, e.g. four ribs. The cylindrical inner wall defines the diameter of the screw to be sectioned wherein the screw comprises, as mentioned above, groove(s) allowing a positive fit between the insert 14 and thus the rotating portion of the cutter 1 and the screw shaft. The embodiment shown comprises four ribs and the screws to be sectioned with this insert have a corresponding diameter and four longitudinal grooves. In other words, the inner wall of insert 14 is allowing the same positive fit as does the inner wall structure of insert 13. Within this embodiment it is only important that the shaft of the screw is in a separate positive fit within both inserts 13 and 14. In order to section shafts of different screws (different diameter, different outer form), the insert 14 can be replaced as shown in FIG. 2. The embodiment of the cutter 1 provides one positive fit for one part of the pin within one insert 13 and a further positive fit for another part of the pin within the other insert 14, wherein the rotation is actuated around the longitudinal axis T of the pin. Since the rotation axis T is identical to the axis of the shaft the positive fit comprises means for locking each shaft portion against rotation relative to the shaft itself.

In a simpler embodiment inserts 13 and 14 can be unitary with the tubular elements 3 and 4, respectively.

Reference numeral 18 relates to a ball with adjacent spring, both being located in a radial bore 28 in element 4. The inner spring pushes on the outer ball which is located inside peripheral opening 28. However, the ball is pushing against the inner wall of the upper portion 27 of insert 14. Four bores in portion 27 of element 4 allow defining four detent positions for the ball extending into one of these bores in portion 27. This allows aligning ribs 9 of inserts 13 and 14, respectively.

The second tubular element 4 comprises a distal through going hollow shaft portion on which the cogwheel 10 is firmly attached as transmission element on the connection portion 12 of element 4. Cogwheel 10 rotates around axis T. Preferably cogwheel 10 is only part of a wheel, covering only a section of a wheel e.g. 90 degrees, since a rotation of the tubular element 4 for about 60 to 90 degrees is sufficient to break the shaft of a pin introduced into elements 13 and 24 at level I. The transmission gear of the cogwheel 10 can cover an angle of between 45 and 120 degrees. Teeth 43 of cogwheel 10 are meshing with corresponding teeth 44 of gear axle 6. Gear axle 6 rotates around rotational axis R which is parallel to longitudinal axis T. Gear axle 6 is mounted in a reception or blind hole 34 within handle 5, preferably comprising a bearing. Handle 5 is therefore positioned in a plane spanned by axes T and R. Gear axle 6 comprises a lower portion allowing a secure bearing within handle 5, e.g. a fastening means 11, a middle gear portion comprising teeth 44 for meshing with cogwheel 10 and an upper portion 8 onto which a turning handle 7 (shown in FIG. 4) is mounted. Fastening means 11 can comprise a circumferential groove in gear axle 6 with a fixating pin through handle 5.

Figure 3:
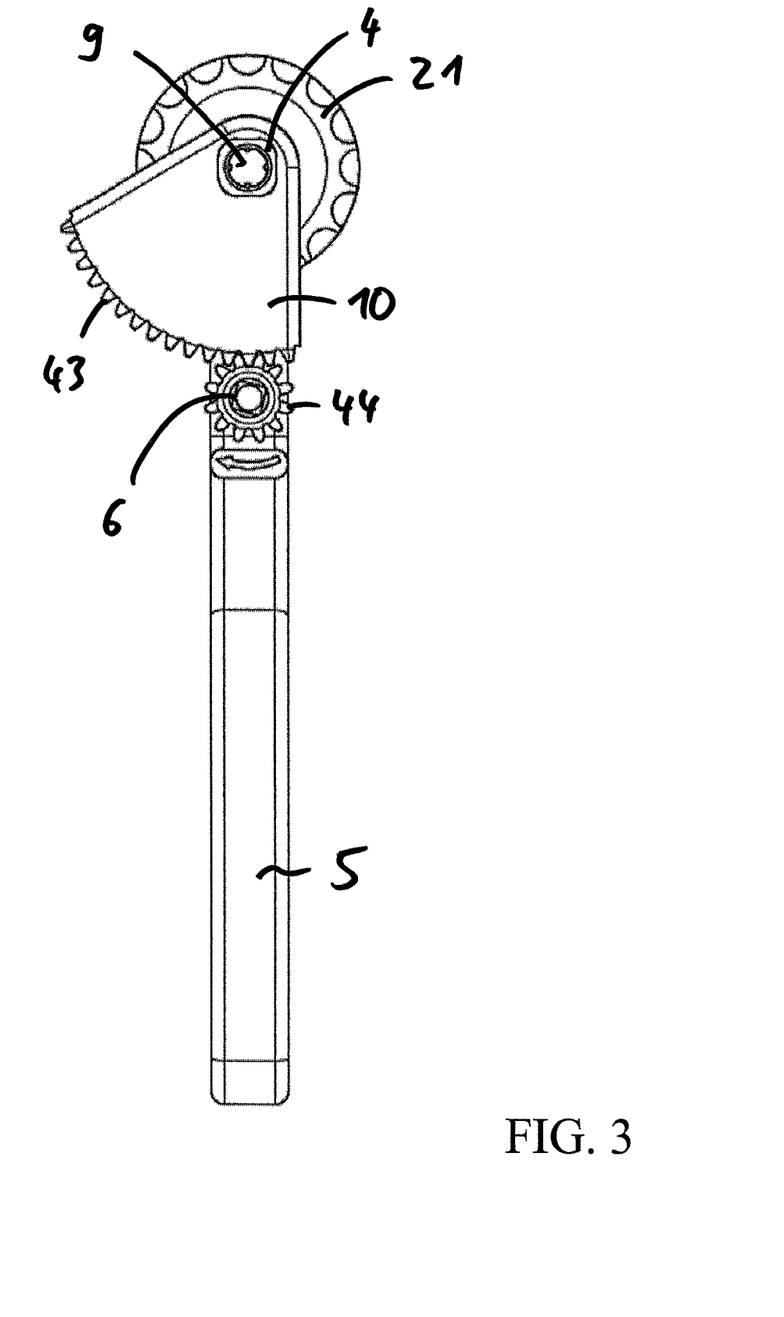
FIG. 3 shows a view from above on the cutter according to FIG. 1.

FIG. 3 shows a view from above of the cutter 1 according to FIG. 1. Identical or similar features receive identical reference numerals in all drawings. FIG. 3 shows the cutter 1 in the parking position or stationary position, i.e. spring 17 is relaxed or under predefined tension in the sense that the inner tubular element 4 engages an abutment within the outer tubular element 3 (not shown in the drawings).

The cogwheel 10 is mounted on the upper connection portion 12 of the outer tubular element 4 which is hollow and therefore FIG. 3 shows a view from above looking down the through bore 2, within which four ribs 9 can be seen in an regular angular arrangement of 90 degrees one from the other. The ribs 9 as seen in FIG. 3 are the ribs 9 of the insert 13 hiding the ribs 9 within insert 14 being in alignment.

Figure 4:
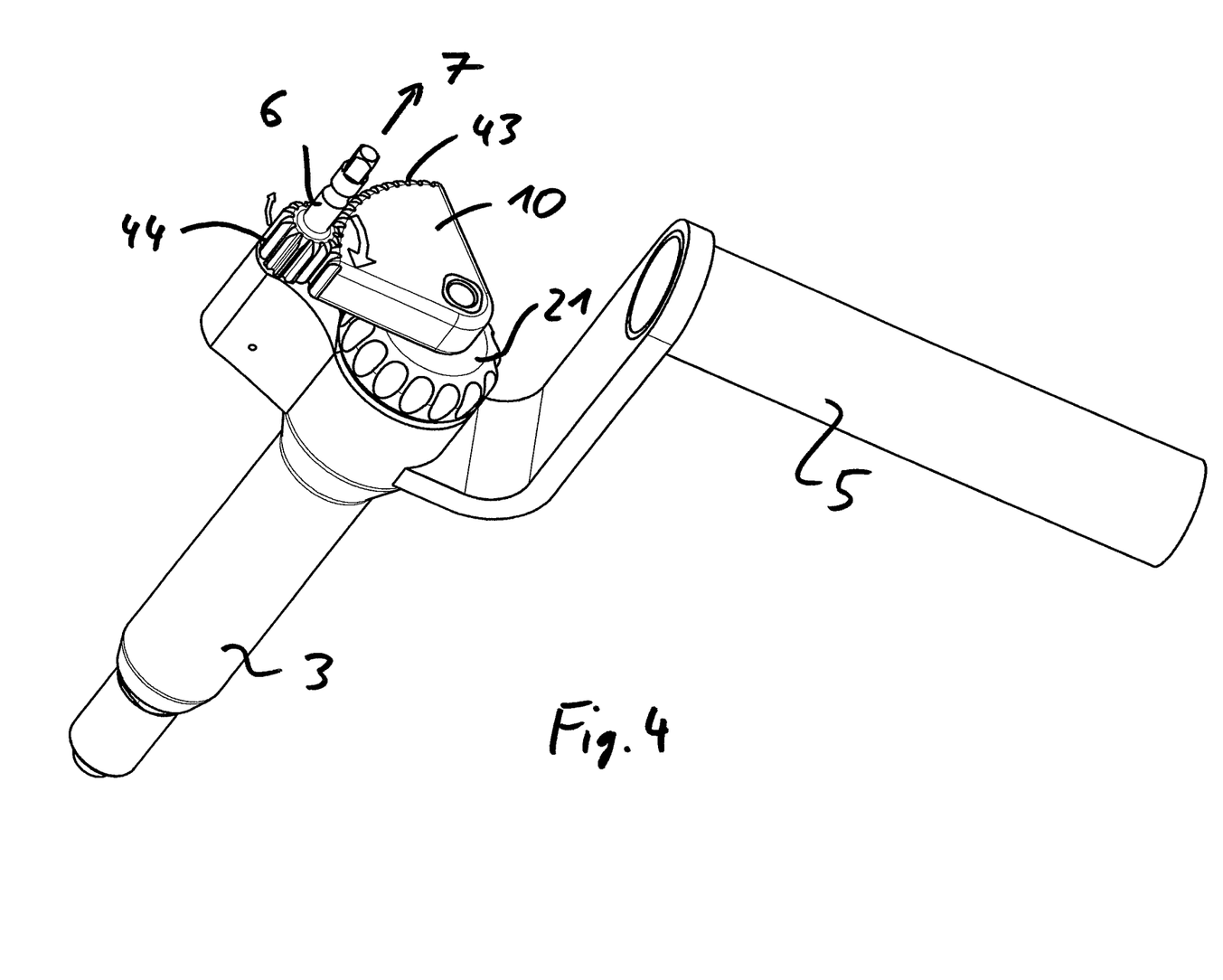
FIG. 4 shows a perspective view of a pin cutter similar to FIG. 1 using a different handle.

Therefore the function of the pin cutter 1 is as follows and can be seen in connection with FIG. 4 showing a perspective view a pin cutter 1 according to FIGS. 1 to 3, wherein a different handle assembly 5 is used. Starting point is a pin introduced in bony material of a patient (not shown in the drawings). Pin cutter 1 is positioned on a long pin to be shortened wherein the pin cutter 1, i.e. the tubular elements 3 and 4 are rotated as a unit around the axis T to allow the ribs 9 of the second gripping unit or locking insert 14 to glide into grooves of the pin. Since the ribs 9 of both inserts 13 and 14 are in alignment the shaft of the screw is advanced until the user of the pin cutter 1 decides that the position of the intended cutting plane I is reached. Then the handle 5 of the stationary portion is in a defined position and held. The user of the pin cutter then rotates the turning handle 7 mounted in prolongation of axis R on axle 6, so that the middle portion of axle 6 with gear teeth 44 is rotating the cogwheel 10 as transmitting element with its teeth 43 as shown in FIG. 4 with respective arrows. Therefore, the inner second tubular element 3 rotates and thus the upper insert 14. Therefore below the plane level I, i.e. proximally of the screw of the pin, the lower portion of the shaft is maintained in position in fix communication with handle 5, wherein distally to the screw and above the plane level I the upper portion of the shaft is rotated and thus separated from the screw portion.

There is no direct yanking movement, since the breaking force is transmitted through a rotation wherein the force is applied coaxially to axis R and has therefore no direct impact on a rotation around axis T. Additionally, the separation has the advantage that the cutter 1 can be taken away from the patient while the cut pin portion remains within the bore 2, since the not aligned ribs 9 prevent the cut portion from sliding out of the lower end nozzle 31.

Figures 5, 6:
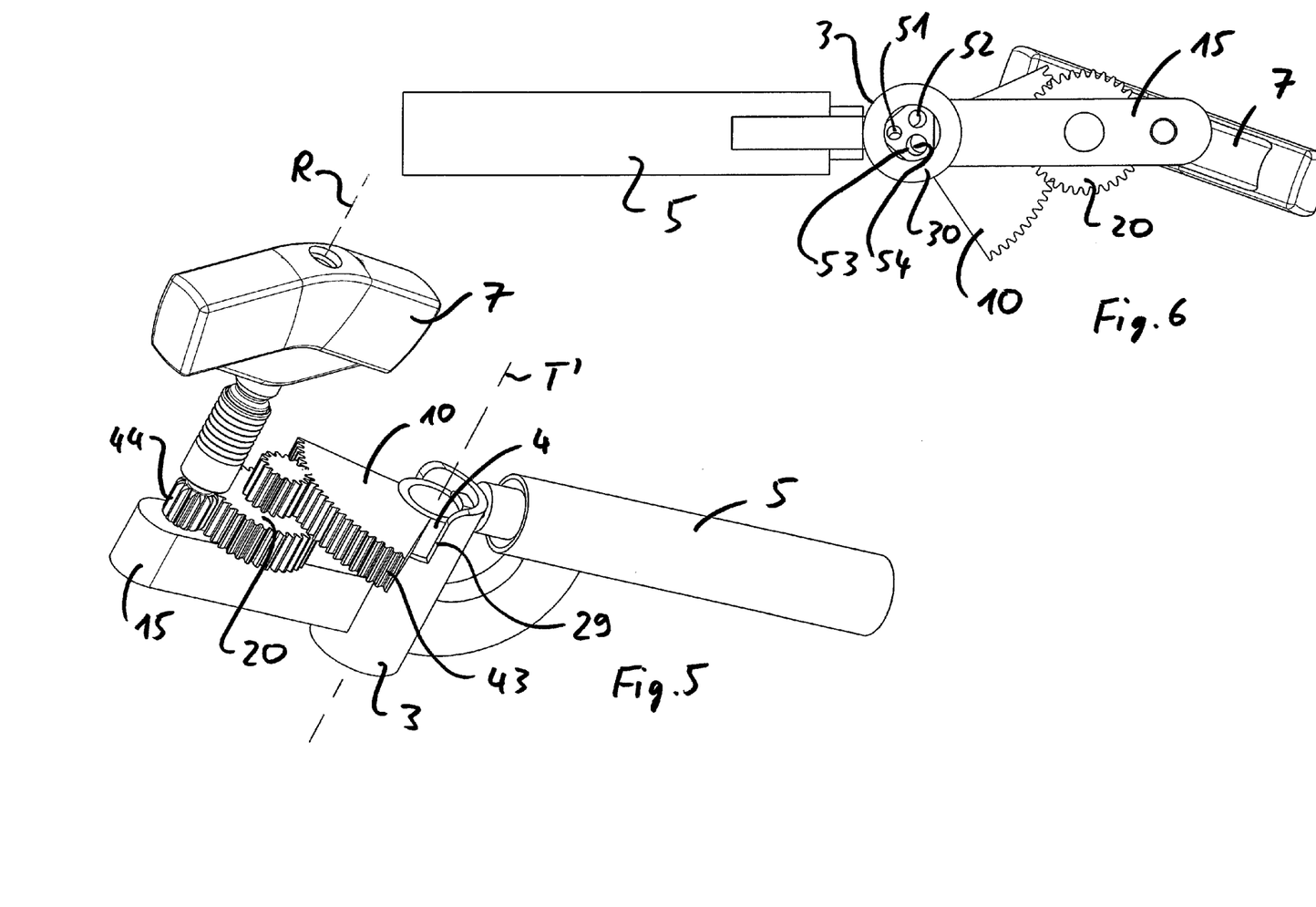
FIG. 5 shows a simplified perspective view from above of a pin cutter according to a second embodiment of the invention in a slightly rotated position.
FIG. 6 shows a view from below on the pin cutter according to FIG. 5.

FIG. 5 shows a simplified perspective view from above of a pin cutter 1 according to a second embodiment of the invention in a slightly rotated position; and FIG. 6 shows a view from below on the pin cutter 1 according to FIG. 5, when the handle 7 is slightly rotated.

Pin cutter 1 comprises as stationary portion of the cutter 1 an outer first tubular element 3 directly attached to handle 5. Opposite to the handle 5, the tubular element 3 comprises a mounting plate 15, within which several bearings are provided for fixing a geared transmission. Turning handle 7 is mounted or unitary with gear axle 6 mounted on plate 15. Teeth of gear 6 mesh with a transmission gear 20 for a gear reduction. Transmission gear 20 mesh with teeth 43 of cogwheel 10. Cogwheel 10 is fixedly connected with the second inner tubular element 4. The upper portions of the side walls 29 of the outer tubular element 3 provide abutments for the cogwheel 10.

Turning handle 7 rotates cogwheel 10 and thus the second inner tubular element 4 of the rotational portion against the first outer tubular element 3 of the stationary portion. FIG. 6 shows the function of the device in detail. As it can be seen from the position of the cogwheel 10, FIG. 6 shows the cutter 1 after having executed a rotation of the cogwheel 10 by about 15 to 30 degrees. Axis of the turning handle R is parallel to the axle 6 and thus in parallel to the common longitudinal axis T' of the tubular elements 3 and 4.

The function of the cutter 1 according to the second embodiment is different in the sense that also cylindrical pins without a structured surface can be sectioned. In other words, the second embodiment of the cutter 1 provides one positive fit for one part of the pin within one tubular element 3 and a further positive fit for another part of the pin within the other tubular element 4, which of course could also be inserts. The rotation is actuated around a longitudinal axis T' being not in line but only parallel to the longitudinal axis T of the pin. This can be seen in FIG. 6. The bottom surface 30 of the outer tubular element 3 comprises three through bores 51, 52 and 53. The three bores 51, 52 and 53 are provided to accommodate three different sizes of pins which can be introduced into a corresponding hole with the least play. Possible diameters of the pins are e.g. 4 mm, 5 mm and 6 mm, wherein the holes have an inner diameter e.g. 0.1 mm larger. If applied to pins to be used fixing bone fragments in (e.g. hand, fore arm or foot surgery) then a sequence of diameters could be 2, 3 and 4 mm, whereas for a different application such a sequence of diameters could be 6, 7 and 8 mm.

In the stationary or parking position, preferably maintained by a spring (not shown) the three holes 51, 52, and in the tubular element 3 are congruent with respective through bores in the inner tubular element 4, i.e. the have the same diameter. In FIG. 6 a through bore 54 is shown behind the through bore 53. Since the turning handle 7 is shown after having been rotated by about 20 to 30 degrees, the three through bores (within which bore 54) of the inner tubular element 4 are rotated by the 20 to 30 degrees amount around axis T'. Therefore the portion of a pin advanced in the through bore of the inner tubular element 4 is cut at the abutment plane between tubular elements 3 and 4. One difference between the first and second embodiment relies on the fact that the rotation of the pin cutter 1 is not effected around the axis T of the pin in the second embodiment.

However, it is possible—according to an embodiment not shown in the drawings—to provide one single central through bore within the underside 30 of the tubular element 3, i.e. along the axis T of the pin, and to provide an inner tubular element 4 with one single through bore which is, in the parking position, congruent with the central through bore of element 3, and which is, when the cogwheel 10 is rotated, rotated around an axis being parallel to axes R and T but not in line with R or T. In other words the rotational axis of the second tubular element 4 is eccentric relative to the axis T of the first tubular element 3 and the pin to be shortened. This can be achieved through mounting the second tubular element 4 with the cogwheel eccentric to axis T.

The cutting tool 1 is preferably made of appropriate materials known to the people skilled in the art. Usually the device is made of stainless steel with components as e.g. the cap and handle in plastic. The cutting inserts 13 and 14 and especially the cutting edges can be in hard metal, carbide or ceramics.

Within a further embodiment, not shown in the drawings, inner and outer tubular elements 3 and 4 comprise complementary threads within at least a portion along the tube. Therefore rotation of the cogwheel 10 is also translated into a relative movement between the tubular elements 3 and 4. Then a sleeve can be disposed radially between the tubular elements 3 and 4, the sleeve having convergent frustroconical surfaces aligned with the gripping components 13, 14 and means for urging the gripping components towards one another over the frustroconical surfaces and thereby radially inwards to engage and grip said shaft in two different portions allowing to perform the twisting motion on a smooth cylindrical shaft. This allows for a separation of the pin along the centre of the frustroconical surfaces as can be seen in FIG. 4 of U.S. Pat. No. 6,928,900, the disclosure of which is incorporated herein by reference.

Figure 7:
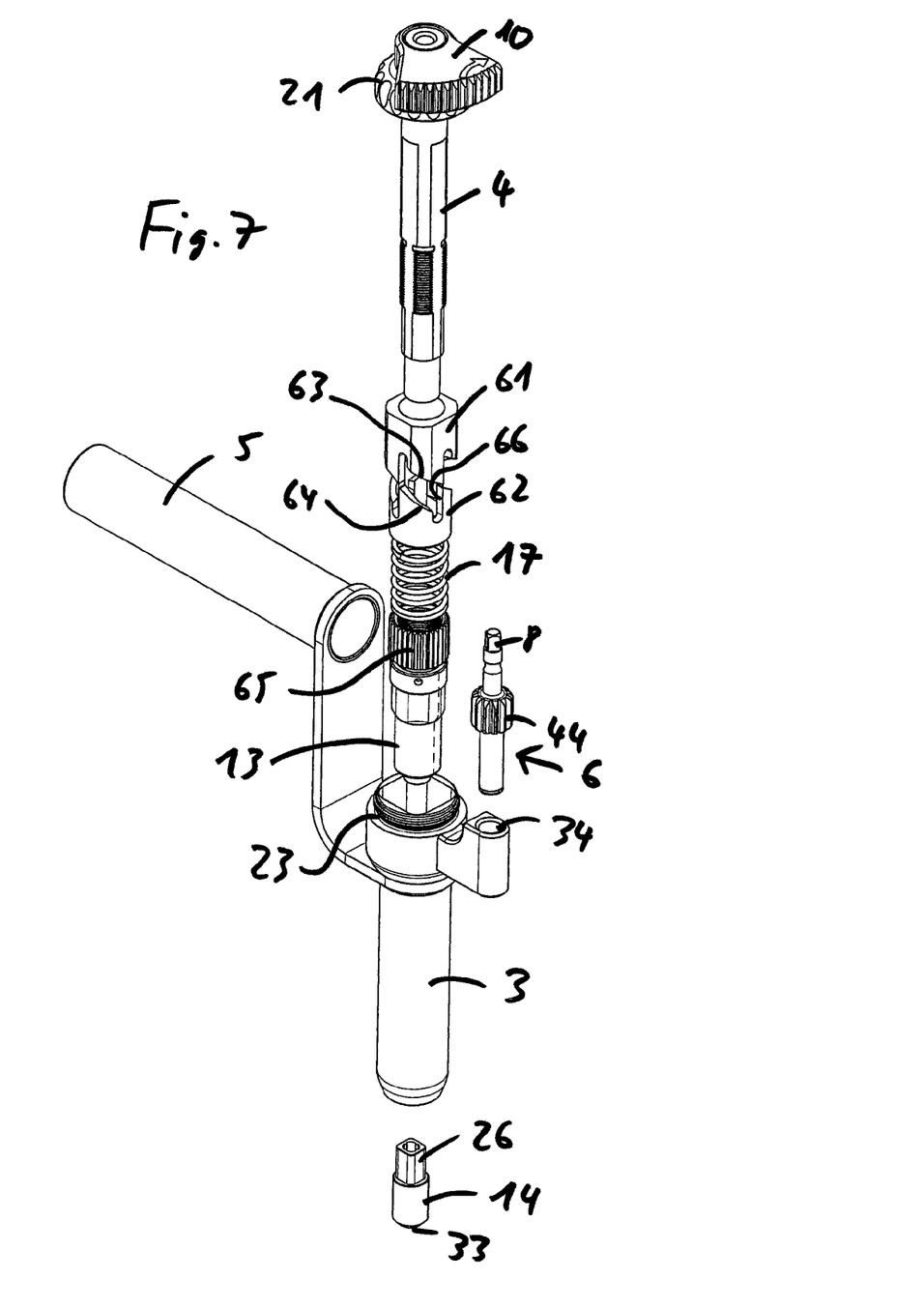
FIG. 7 shows an exploded perspective view of a pin cutter according to a third embodiment of the invention having a different zero position mechanism.

Finally FIG. 7 shows an exploded perspective view of a pin cutter according to a third embodiment of the invention having a different zero position mechanism. Second tubular element 4 comprises an outer square profile engaging a complementary profile in rotating element 62. Rotating element is a sleeve comprising at its circumference four angularly separated tangentially inclined surfaces 64, i.e. covering 90 degrees with a longitudinal oriented connection slope 66. A blocking element 61 is positioned distal to the rotating element and comprises complementary inclined surfaces 63. Blocking element 61 has an outer square profile engaging a complementary profile within the outer tubular element 3. On the opposite side of the blocking element 61 spring 17 is located abutting against nut 65, which is fixed inside the device 1 by being screwed on the inner tubular element 4. Nut 65 is located at a specific position along the longitudinal axis T. Turning the inner tubular element 4 rotates element 62, which is pushed against blocking element 61. Element 62 is gliding along longitudinal axis of tubular element 4 against the force of spring 17 until a zero position is reached, when the two elements 61 and 62 are closing along the connection slope 66. For easy reference insert is shown below tubular element 3, although it is mounted inside insert 3.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A tool for breaking a shaft, comprising a first tubular element comprising an inner through bore adapted to receive a first portion of said shaft in a first position of said tool, a second tubular element comprising an inner through bore adapted to receive a further second portion of said shaft in said first position of said tool, a first handle and a drive element, wherein the first tubular element is connected to the first handle, wherein the second tubular element is connected to the drive element, wherein a longitudinal axis of said first tubular element, a longitudinal axis of said second tubular element as well as an axis of the shaft to be broken are parallel one to the other, wherein the second tubular element has a distal surface being in contact with a neck surface of the first tubular element forming a shearing plane perpendicular to said parallel axes, wherein, starting from said first position, a rotation between the first tubular element and the second tubular element around one of their longitudinal axes creates a twisting movement of the second shaft portion received in the second tubular element relative to the first shaft portion received in the first tubular element and shears the shaft portions at the interface between them, the first handle is fixedly connected to the first tubular element, the drive element is mounted on the first tubular element for a rotation around an axis parallel to said longitudinal axis of the shaft, the drive element comprising a gear engaging the second tubular element for transmittal of a rotation of the gear into a rotation of the second tubular element for said twisting movement, wherein the drive element gear is mounted offset from the second longitudinal axis, wherein the drive element is rotatably driven by a T-shaped handle spaced proximally of a proximal surface of the distal second tubular element, which proximal surface is spaced from the distal surface of the second tubular element.

2. The tool according to claim 1, wherein the drive element comprises an axle having the gear mounted thereon to mesh with a transmission gear mounted with the second tubular element.

3. The tool according to claim 2, wherein the transmission gear is a cogwheel having a toothed sector covering an angle of between 45 and 120 degrees.

4. The tool according to claim 2, wherein the drive element is mounted on the first handle.

5. The tool according to claim 1, wherein a spring is mounted between the first tubular element and the second tubular element adapted to rotate the second tubular element into said first position.

6. The tool according to claim 5, wherein the spring is arranged within the first tubular element and concentrically with the second tubular element.

7. The tool according to claim 1, wherein the inner through bore of the first tubular element adapted to receive said first portion of said shaft is coaxially aligned along a longitudinal axis of the tool.

8. The tool according to claim 7, wherein the inner through bores of the first and second tubular elements comprise positive locking elements adapted to lock each shaft portion against rotation relative to the shaft itself, wherein said positive locking elements are aligned in the first position.

9. The tool according to claim 1, wherein the drive element gear is rotatable about a rotational axis arranged parallel to and offset from the longitudinal axes of the first and second tubular elements.

10. The tool according to claim 1, wherein the first tubular element comprises a first insert having said inner through bore adapted to receive said first portion of said shaft and wherein the second tubular element comprises a second insert having said inner through bore adapted to receive said further second portion of said shaft, wherein the first insert and the second insert have juxtaposed surfaces for a positive fit with the first and second tubular element, respectively.

11. The tool according to claim 1, wherein said shearing rotation is actuated around the longitudinal axis of the pin, wherein said inner through bore of the first tubular element provides a first positive fit for the first portion of the shaft and said inner through bore of the second tubular element provides a positive fit for the second portion of said shaft, wherein the positive fit is adapted to lock each shaft portion against rotation about the longitudinal axis.

12. The tool according to claim 1, wherein said gear comprises a reduction gear.

13. The tool according to claim 1, wherein the first tubular element comprises at least one inner through bore along an axis eccentric relative to the longitudinal axis of the first tubular element, wherein the second tubular element comprises, in the first position, at least one corresponding inner through bore along an axis eccentric relative to the longitudinal axis of the first tubular element.

14. The tool according to claim 1, wherein the first tubular element comprises one inner through bore along the longitudinal axis of the first tubular element, wherein the second tubular element comprises, in the parking position, at least one corresponding inner through bore along said first tubular element axis, wherein the longitudinal axis of the second tubular element is eccentric relative to the longitudinal axis of the first tubular element.

15. A tool for breaking a shaft comprising:
a first tubular element having a bore for receiving a first shaft portion extending along a first longitudinal axis;
a second tubular element having a bore for receiving a second shaft portion extending along a second longitudinal axis rotatably mounted with respect to the first tubular element;
a first handle connected to the first tubular element and a drive element connected to the second tubular element;
wherein the longitudinal axis of said first tubular element, the longitudinal axis of said second tubular element as well as a third longitudinal axis of a shaft to be broken are parallel one to the other, wherein a distal surface of the second tubular element is in contact with a surface of the first tubular element forming a shearing plane perpendicular to said parallel axes, wherein, starting from a first position, a rotation between the first tubular element and the second tubular element around one of these axes creates a relative movement about the third longitudinal axis between the second shaft portion received in the second tubular element bore and the first shaft portion received in the first tubular element bore thereby shearing the shaft portions at the shearing plane wherein the drive element is mounted offset, from the longitudinal axis of the second tubular element, wherein the drive element is driven by a T-shaped handle spaced proximally from a proximal surface of the second tubular element.

16. The tool of claim 15 wherein the first handle is mounted on the first tubular element for a rotation of the first tubular element around the first longitudinal axis, wherein the drive element is a gear engaging the second tubular element for transmittal of a rotation to the second tubular element for producing the relative movement.

17. The tool according to claim 16, wherein the drive element comprises an axle having the gear mounted thereon to mesh with a transmission gear mounted with the second tubular element.

18. The tool according to claim 17, wherein the transmission gear is a cogwheel covering an angle of between 45 and 120 degrees.

19. The tool according to claim 17, wherein said gear comprises a reduction gear.

20. The tool according to claim 15, wherein a spring is mounted between the first tubular element and the second tubular element adapted to rotate the second tubular element into said first position.

21. The tool according to claim 20, wherein the spring is a leg-spring arranged within the first tubular element and concentrically with the second tubular element.

22. The tool according to claim 15, wherein the first longitudinal axis of the bore of the first tubular element is adapted to receive said first portion of said shaft is coaxially aligned along the third longitudinal axis.

23. The tool according to claim 22, wherein the inner through bores of the first and second tubular elements further comprise positive locking elements adapted to lock each shaft portion against relative rotation, wherein said positive locking elements are aligned in said first position to allow insertion of the shaft.

24. The tool according to claim 15, wherein the drive element is rotatable about a rotational axis arranged parallel to the longitudinal axes of the first and second tubular elements.

25. The tool according to claim 24, wherein the rotational axis of the drive element is arranged parallel and offset to the longitudinal axes of the first and second tubular elements.

26. The tool according to claim 15, wherein the first tubular element comprises a first insert having the through bore adapted to receive the first shaft portion and wherein the second tubular element comprises a second insert having the bore adapted to receive the second shaft portion, wherein the first insert and the second insert have juxtaposed surfaces producing a non-rotational positive fit with the first and second tubular element, respectively.

27. The tool according to claim 26, wherein the shearing rotation is actuated around the longitudinal axis of the shaft, wherein the bore of the first tubular element provides a first positive fit for the first shaft portion and the bore of the second tubular element provides a second positive fit for the second shaft portion, wherein the positive fit is adapted to lock each shaft portion against rotation.

28. A tool for breaking a shaft, comprising a first tubular element comprising an inner through bore adapted to receive a first portion of said shaft in a first position of said tool, a second tubular element comprising an inner through bore adapted to receive a further second portion of said shaft in said first position of said tool, a first handle and a drive element, wherein the first tubular element is connected to the first handle, wherein the second tubular element is connected to the drive element, wherein a longitudinal axis of said first tubular element, a longitudinal axis of said second tubular element as well as an axis of the shaft to be broken are parallel one to the other, wherein the second tubular element has a bottom surface being in contact with a neck surface of the first tubular element forming a shearing plane perpendicular to said parallel axes, wherein, starting from said first position, a rotation between the first tubular element and the second tubular element around one of their longitudinal axes creates a twisting movement of the second shaft portion received in the second tubular element relative to the first shaft portion received in the first tubular element and shears the shaft portions at the interface between them, the shaft and the first tubular member have mating radially extending elements that prevent relative rotation therebetween, the first handle is fixedly connected to the first tubular element, the drive element is mounted on the first tubular element for a rotation around an axis parallel to said longitudinal axis of the shaft, the drive element comprising a gear engaging the second tubular element for transmittal of a rotation of the gear into a rotation of the second tubular element for said twisting movement, wherein the drive element is mounted offset from the longitudinal axis of the second tubular element.

* * * * *